United States Patent
Ahluwalia

(10) Patent No.: US 9,744,276 B2
(45) Date of Patent: Aug. 29, 2017

(54) SUCTION DEVICE

(71) Applicant: Prabhat Kumar Ahluwalia, Little Falls, NY (US)

(72) Inventor: Prabhat Kumar Ahluwalia, Little Falls, NY (US)

(*) Notice: Subject to any disclaimer, the term of this patent is extended or adjusted under 35 U.S.C. 154(b) by 0 days.

(21) Appl. No.: 14/572,843

(22) Filed: Dec. 17, 2014

(65) Prior Publication Data

US 2016/0175496 A1 Jun. 23, 2016
US 2017/0000932 A9 Jan. 5, 2017

Related U.S. Application Data

(63) Continuation of application No. 13/847,347, filed on Mar. 19, 2013, now Pat. No. 8,945,093.

(60) Provisional application No. 61/613,219, filed on Mar. 20, 2012.

(51) Int. Cl.
*A61M 1/00* (2006.01)

(52) U.S. Cl.
CPC .......... *A61M 1/008* (2013.01); *A61M 1/0035* (2014.02); *A61M 1/0039* (2013.01); *A61M 1/0045* (2014.02); *A61M 1/0064* (2013.01); *A61M 1/0084* (2013.01)

(58) Field of Classification Search
CPC .......... A61M 1/00; A61M 27/00; A61F 13/00; A61F 13/02
See application file for complete search history.

(56) References Cited

U.S. PATENT DOCUMENTS

| 1,317,851 | A | | 10/1919 | Arnett |
| 2,243,299 | A | | 5/1941 | Travers |
| 2,531,793 | A | | 11/1950 | Sulek |
| 3,421,510 | A | * | 1/1969 | Kettenbach ......... A61M 1/0084 |
| | | | | 604/268 |

(Continued)

FOREIGN PATENT DOCUMENTS

| EP | 0613387 | 9/1994 |
| WO | WO-8500016 | 1/1985 |

(Continued)

OTHER PUBLICATIONS

Conmed Endosurgery, "Universal Plus, Electrosurgical and High Volume Suction/Irrigation Systems for Surgical Endoscopy," 2011 4 pages.

(Continued)

*Primary Examiner* — Adam Marcetich
(74) *Attorney, Agent, or Firm* — Pierson IP, PLLC

(57) ABSTRACT

An embodiment includes a suction device handle for use with a vacuum supply conduit to suction a fluid or tissue, the handle comprising: a hand-grippable body defining a chamber; the hand-grippable body comprising a distal end configured to support a suction tip; the suction tip including a distal end of a vacuum supply conduit extending within an outer cannula, the vacuum supply conduit being offset from a distal end of the outer cannula by a predetermined distance; wherein the distal end of the hand grippable body is connected to a proximal end of the outer cannula and the chamber is connected in fluid communication with the suction pressure or vacuum generated at the distal end of the vacuum supply conduit. Additional embodiments are described herein.

20 Claims, 2 Drawing Sheets

(56) References Cited

U.S. PATENT DOCUMENTS

| | | | | |
|---|---|---|---|---|
| 3,469,582 | A | 9/1969 | Jackson | |
| 3,771,522 | A | 11/1973 | Waysilk et al. | |
| 3,771,527 | A | 11/1973 | Ruisi | |
| 3,912,168 | A | 10/1975 | Mullins et al. | |
| 3,952,743 | A | 4/1976 | Harrison | |
| 3,958,566 | A | 5/1976 | Furihata | |
| 4,361,187 | A | 11/1982 | Luers | |
| 4,400,168 | A | 8/1983 | Buechel et al. | |
| 4,468,217 | A | 8/1984 | Kuzmic et al. | |
| 4,487,600 | A | 12/1984 | Brownlie | |
| 4,553,957 | A | 11/1985 | Williams | |
| 4,648,871 | A | 3/1987 | Jacob | |
| 4,661,110 | A * | 4/1987 | Fortier | A61M 39/20 604/256 |
| 4,680,026 | A * | 7/1987 | Weightman | A61M 1/0064 433/84 |
| 4,692,140 | A | 9/1987 | Olson | |
| 4,776,840 | A * | 10/1988 | Freitas | A61M 3/0262 604/118 |
| 4,935,006 | A | 6/1990 | Hasson | |
| 4,941,872 | A | 7/1990 | Felix et al. | |
| 4,998,527 | A | 3/1991 | Meyer | |
| 5,186,714 | A | 2/1993 | Boudreault et al. | |
| 5,188,591 | A | 2/1993 | Dorsey, III | |
| 5,195,958 | A * | 3/1993 | Phillips | A61B 18/1482 604/21 |
| 5,195,959 | A | 3/1993 | Smith | |
| 5,203,769 | A | 4/1993 | Clement et al. | |
| 5,224,929 | A | 7/1993 | Remiszewski | |
| 5,254,083 | A * | 10/1993 | Gentelia | A61M 1/0064 251/7 |
| 5,261,905 | A | 11/1993 | Dorsey, III | |
| 5,281,201 | A | 1/1994 | Dorsey, III | |
| 5,295,956 | A | 3/1994 | Bales et al. | |
| 5,324,254 | A | 6/1994 | Phillips | |
| 5,348,555 | A | 9/1994 | Zinnanti | |
| 5,349,950 | A | 9/1994 | Ulrich et al. | |
| 5,350,356 | A | 9/1994 | Bales et al. | |
| 5,391,145 | A | 2/1995 | Dorsey, III | |
| 5,409,013 | A | 4/1995 | Clement | |
| 5,464,390 | A | 11/1995 | Arnett et al. | |
| 5,605,537 | A * | 2/1997 | Ivey | A61B 17/3203 604/21 |
| 5,830,214 | A | 11/1998 | Flom et al. | |
| 6,155,824 | A | 12/2000 | Kamen | |
| 6,156,004 | A | 12/2000 | Tremaine et al. | |
| 6,423,028 | B1 * | 7/2002 | Gonon | A61B 17/3203 604/28 |
| 6,508,823 | B1 * | 1/2003 | Gonon | A61B 17/3203 200/81 H |
| 6,723,069 | B1 | 4/2004 | Weldon et al. | |
| 7,955,318 | B1 | 6/2011 | Schultz et al. | |
| 2001/0002432 | A1 | 5/2001 | Bugge | |
| 2003/0036723 | A1 | 2/2003 | Henniges et al. | |
| 2003/0167053 | A1 | 9/2003 | Taufig | |
| 2004/0082906 | A1 | 4/2004 | Tallarida et al. | |
| 2005/0027165 | A1 * | 2/2005 | Rovegno | A61B 1/012 600/154 |
| 2005/0197645 | A1 | 9/2005 | Karpowicz et al. | |
| 2006/0100605 | A1 | 5/2006 | Bicakci et al. | |
| 2007/0156083 | A1 | 7/2007 | Johnston et al. | |
| 2008/0121236 | A1 | 5/2008 | Field | |
| 2008/0249553 | A1 | 10/2008 | Gruber et al. | |
| 2009/0018531 | A1 | 1/2009 | Welches et al. | |
| 2010/0010431 | A1 | 1/2010 | Tulley | |
| 2010/0198170 | A1 | 8/2010 | Umeda et al. | |
| 2011/0023884 | A1 | 2/2011 | Cuevas et al. | |
| 2011/0144571 | A1 | 6/2011 | Ahluwalia | |

FOREIGN PATENT DOCUMENTS

| | | |
|---|---|---|
| WO | WO-86-04247 | 7/1986 |
| WO | WO-93/17733 | 9/1993 |
| WO | WO-94/13335 | 6/1994 |
| WO | WO-94/19030 | 9/1994 |
| WO | WO-94/23773 | 10/1994 |
| WO | WO-2009014026 | 1/2009 |

OTHER PUBLICATIONS

Covidien Surgical, "Surgiwand II 5mm," www.covidien.com/autosuture; 2012, 1 page.

Vectect, "Medical Expo, The Online Medical Devices Exhibition," Laparoscopic Surgery Suction/Irrigation Cannula, 2013, 2 pages.

European Search Report for EP 13764182 dated Oct. 29, 2015.

* cited by examiner

SUCTION DEVICE

This application claims priority to U.S. Provisional Patent Application No. 61/613,219 filed on Mar. 20, 2012 and entitled "Suction Device", and this application claims a benefit under 35 U.S.C. §120 of prior filed Non-Provisional application Ser. No. 14/847,347 filed on Mar. 19, 2013 which are fully incorporated herein by reference in its entirety.

BACKGROUND

U.S. Pat. App. Publication No. 2011/0144571 entitled SUCTION DEVICE filed on Oct. 14, 2010 ("the '571 application") shares a common inventor with the present application. The '571 application is hereby incorporated by reference. The '571 application discloses a suction device including an outer tube and an inner suction tube. The inner suction tube is offset a distance from an inlet of the outer suction tube. The offset distance facilitates its use in surgical (and other) suction activities with reduced risk of clogging.

Healthcare personnel desire further improvements in suction devices, especially for laproscopic procedures, to facilitate effective removal of tissues and fluids from the surgical site.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an" and "the" include plural referents unless the context clearly dictates otherwise. The term "comprising" and variations thereof as used herein is used synonymously with the term "including" and variations thereof and are open, non-limiting terms.

Figure 1:
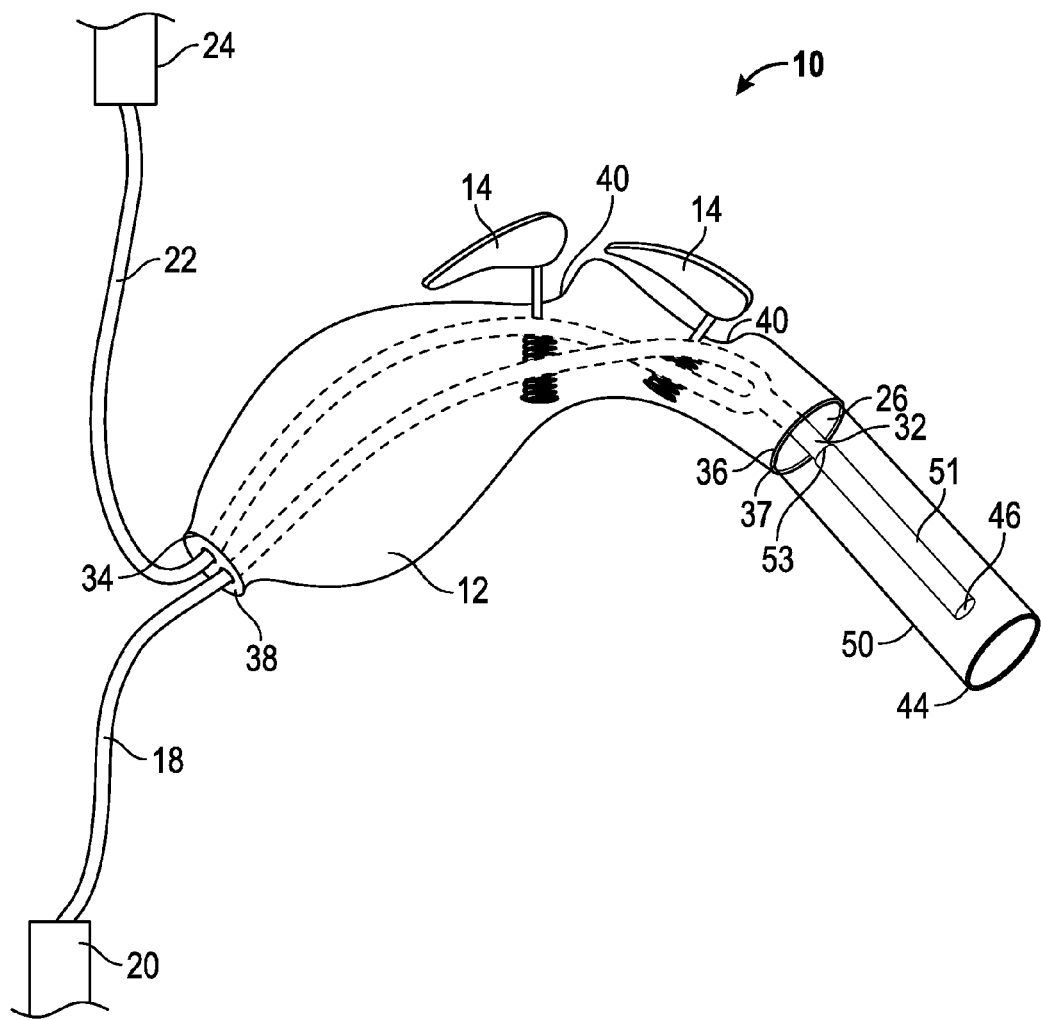
FIG. 1 is a schematic view of a suction device, including a handle.

FIG. 1 shows a suction device 10 of the present invention including a hand-grippable body 12, a plurality of buttons 14, and a suction tip. The body defines a chamber or passage 26. A vacuum supply conduit 18 connected to a vacuum supply 20 and an irrigation fluid supply conduit 22 connected to a fluid supply 24 may pass through the passage 26. Advantageously, the chamber or passage 26 may facilitate generation of suction or negative pressure by attachment to a suction tip, when the suction tip is in contact with fluid, tissue or any surface.

Figure 2:
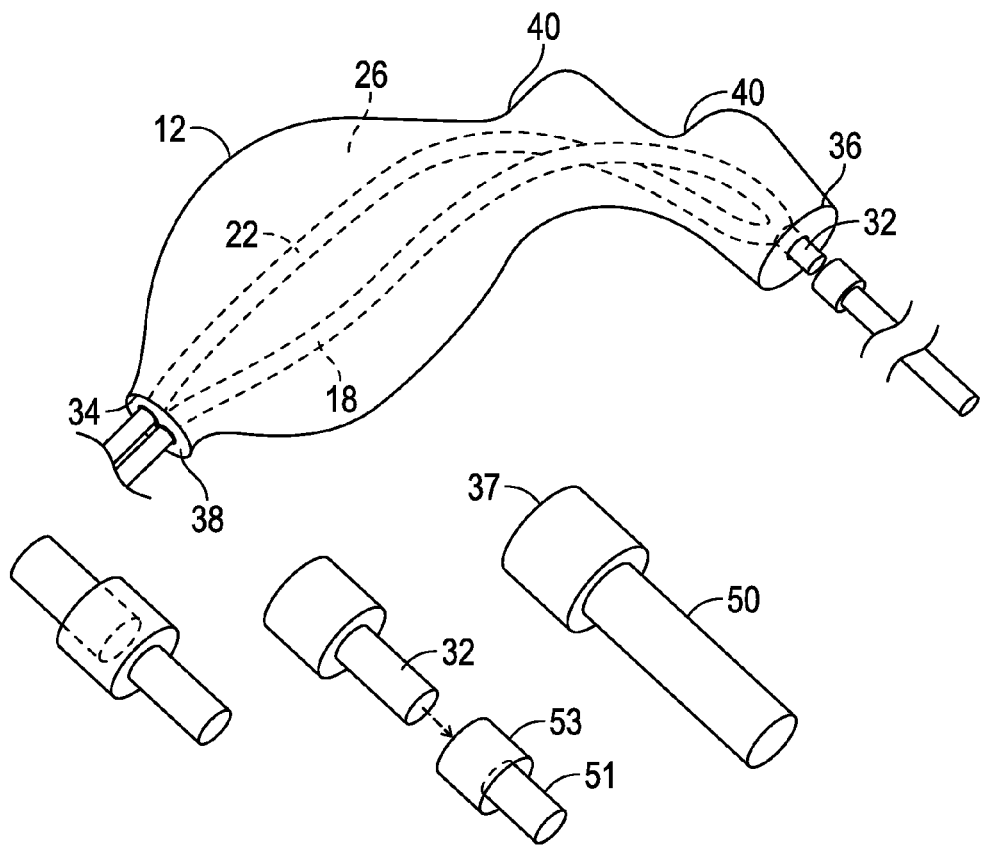
FIG. 2 is a schematic view of the suction device of FIG. 1 being attached to nested suction cannulae.

For example, as shown in FIGS. 1 and 2, the suction tip may include an outer cannula 50 and an inner cannula 51. The outer cannula 50 may have a proximal end 37 and a distal tip 44. The inner cannula 51, which conducts a vacuum supply, extends within the outer cannula 50. The inner cannula 51 also may have a proximal end 53 and a distal tip 46. But, the distal tip 46 of the inner cannula 51 is recessed inwardly from the distal tip 44 of the outer cannula 50. Any and all space defined between the outer cannula 50 and inner cannula 51 that contains a vacuum may be a first suction volume.

Attachment of the suction tip to the body 10, as described in more detail below, establishes fluid communication between the chamber or passage 26 and the suction volume. When fluid communication is established, the chamber or passage 26 may become an additional or second suction volume. Advantageously, a vacuum generated by the inner cannula 51 at its distal tip 46 extends through the suction volume defined between the inner cannula 51 and outer cannula 50 and into the chamber 26 defined in the body 12. Further advantageously, the recessed position of the inner cannula 51 distal tip 46 helps to break blockages from fluids and tissue being suctioned from the surgical site. Additional details about the structure and operation of the suction tip are described in the '571 application.

The fluid supply 24 may be a bag of saline, for example, under pressure due to the head generated by its elevation above the suction device 10 on a pole. Or, it may be supplied as a standard fluid in an operating room or other healthcare setting. This pressure facilitates urging the fluid down the fluid supply line 22 so as to facilitate suction.

The fluid supply conduit 22 may be polymer or rubber medical tubing, for example, that is configured to direct and control fluid flow to the body 12. At the same time, some flexibility of the tubing is advantageous in order to allow its connection to and passage through the passage defined by the body 12.

The vacuum supply conduit 18 may be of similar construction, although it may have characteristics better adapted to resisting collapse than elevated pressures.

The vacuum supply 20 may be generated by a standalone device, such as a portable pump, or may be part of an existing built-in vacuum or suction pressure supply in the clinical setting. Also, the vacuum supply 20 may include some type of catch basin or other container to capture and hold suctioned fluids and tissues for later safe disposal.

As shown in FIGS. 1 and 2, the conduits 18, 22 may extend through the passage 26 and merge into a single distal conduit end 32. This merger combines the fluid for irrigation with the vacuum so, if both lines are free-flowing, the majority of the irrigation fluid is sucked into the vacuum conduit 18. If only the irrigation conduit 18 is flowing, the conduit 18 supplies fluid at the distal conduit end 32 to dilute tissue, blood or and other bodily fluids. This allows tissue and fluid entering the distal conduit end 32 to be diluted before being sucked up through the vacuum conduit 18, when activated, for disposal.

As shown in FIG. 2, the proximal end 37 of the outer cannula 50 may include a connector. Also, the proximal end 53 of the inner cannula 51 may include a connector. For example, each of the cannulae proximal ends 37 and 53 may have one-half of an appropriately-sized luer, bayonet or other style lock or connector. The other half of the 20 connector may be positioned on the distal end of the body 12 and the single distal conduit end 32. Connecting these connectors will attach the cannulae to the body and conduit, as shown in FIG. 1.

Figure 3:
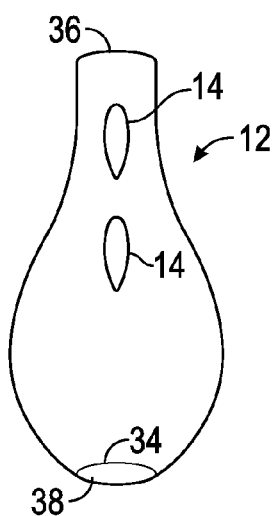
FIG. 3 is a plan view of a body of the suction device of FIG. 1.

As shown in FIG. 3, the body 12 of the suction device may have an ergonomic shape, such as an eggplant or teardrop shape, with a resulting greater volume defined in a portion of the passage 26 proximal of the midline (i.e., half way between the proximal and distal ends) of the body. This shape is configured to facilitate easy gripping and manipulation in a normal range of hand sizes. The body 12 may be constructed of a polymer material so as to be light and inexpensive. Its outer surface may be textured for further ease of gripping and manipulation. The greater volume of the teardrop shape may facilitate the generation of suction or negative pressure in the volume between the inner cannula 51 and outer cannula 50 when the outer cannula 44 is in contact with fluid or tissue.

As shown in FIGS. 1 and 2, the body 12 may also include a neck region that extends out of the bulbous proximal region and then curves gently downward over a region where the fingers would wrap. Restated, the fingers of the hand would wrap around and under the inner curvature. The thumb would be positioned near the buttons 14.

The body 12 includes a proximal end 34 and the distal end 36. At the proximal end may be an air-tight sealing disc 38, as shown in FIG. 1. The sealing disc 38 may be a rubber or polymer plug, for example, that friction fits within a cylindrical opening at the proximal end 34. Defined through the sealing disc 38 may be a pair of holes configured to allow snug passage of the conduits 18, 22. Separate construction of the sealing disc 38 facilitates its removal and replacement along with threading new conduits 18, 22. Also, revealing the opening at the proximal end 34 facilitates cleaning and sterilization of the passage 26 of the body 12.

The distal end 36 defines its own cylindrical opening that, as shown in FIG. 2, may be configured to receive the similarly-sized connector on the proximal end of the outer cannula 50. The opening at the distal end 36 may include its own stopper or member to support in a central location, and allow passage therethrough, of the single distal conduit end 32. Central positioning may facilitate attachment of the conduit end 32 to the proximal end of the inner cannula 51.

Referring again to FIG. 1, the buttons 14 are on the dorsal outer curvature of the body 12 so as to be positioned for thumb actuation. The buttons 14 include shafts or posts that extend through sealed openings in the body 12 so as to prevent air escape. Each of the buttons 14 is spring biased on its shaft to clamp shut on or open a respective one of the conduits 18 or 22.

Depression of the buttons 14 against the spring bias progressively opens the conduits 18 and 22. Progressive opening results in progressively increasing supply of fluid or suction. Linear, adjacent positioning of the buttons 14 on the dorsal surface (as shown in FIG. 3) of the body 12 facilitates simultaneous, dual compression to route some irrigation and vacuum at the same time. Isolated suction or irrigation may also be performed by depressing only one of the buttons 14.

The suction device 10 may also include a single button or more than two buttons for selective application of various combinations of suction and fluids. A single button may be used to actuate a single suction line. Multiple buttons may be used for different types of fluids through different conduits.

The buttons 14, for example, may include compression members such as pyramidal members that trap the flexible conduits 18 or 22 against the inner surface of the body 12 under compression of the spring. Also, the buttons themselves may have an ergonomic shape of a tear drop and be nested within shaped recesses 40 on the dorsal, outer curvature of the body 12.

The chamber or passage 26 is defined within the body 12 by the wall structure of the body. Advantageously, the passage 26 is configured to allow positioning and passage of the conduits 18 and 22 in a configuration that allows their selective compression by the buttons 14. For example, as shown in FIGS. 1 and 2, the conduits 18 and 22 may be configured in a crossing or overlapping configuration that facilitates positioning of the buttons 14 along the mid-dorsal line of the body 12.

The passage 26 has the same general shape as the outer surface of the body 12 due to the relatively consistent wall thickness of the body. However, the passage 26 could have a less similar shape, such as a curved cylinder. Regardless, the passage 26 can extend from the proximal end 34 to the distal end 36 of the body 12 so as to guide and shield the conduits 18 and 22 from entanglement or exposure to the environment.

A number of aspects of the systems, devices and methods have been described. Nevertheless, it will be understood that various modifications may be made without departing from the spirit and scope of the disclosure. Accordingly, other aspects are within the scope of the following claims.

10 suction device
12 body
14 buttons
18 vacuum supply conduit
20 vacuum supply
22 fluid supply conduit
24 fluid supply
26 passage
32 single distal conduit end
34 proximal end
36 distal end
37 outer cannula proximal end
38 sealing disc
40 shaped recesses
44 outer cannula distal tip
46 inner cannula distal tip
50 outer cannula
51 inner cannula
53 inner cannula proximal end That which is claimed:

1. A suction device handle to use with a vacuum supply conduit to suction a fluid or tissue, the handle comprising:
   a hand-grippable body defining a chamber and comprising a distal end configured to support a suction tip;
   the suction tip including a distal end of the vacuum supply conduit extending within an outer cannula, the vacuum supply conduit being offset from a distal end of the outer cannula by a predetermined distance and configured to couple to a vacuum supply, wherein the vacuum supply conduit includes a merging of an irrigation supply conduit and the vacuum supply conduit; and
   a connecting portion configured to couple the distal end of the body to the suction tip;
   wherein the distal end of the body is configured to couple to a proximal end of the outer cannula and the chamber is configured to couple in fluid communication with suction pressure generated at the distal end of the vacuum supply conduit by the vacuum supply;
   wherein the vacuum supply conduit, when coupled to the vacuum supply, forms the suction pressure (a) at a location including within an annular space directly between an outer wall surface of the vacuum supply conduit and an inner wall surface of the outer cannula, (b) within a portion of the chamber located proximal to the location, and (c) that sucks fluid away from the outer cannula and into the vacuum supply conduit, wherein the annular space forms a passageway from the chamber to the distal end of the outer cannula, and the outer wall surface of the vacuum supply conduit and the inner wall surface of the outer cannula are offset from each other due to the annular space;

wherein the vacuum supply conduit is configured to pass through the chamber into the suction tip.

2. A suction device of claim 1, wherein the chamber is further configured to pass a fluid supply conduit.

3. A suction device of claim 2, wherein the chamber is configured to hold the vacuum supply conduit and fluid supply conduit in an overlapping configuration.

4. A suction device of claim 2, wherein a proximal end of the hand grippable body is configured to form an airtight seal around the vacuum supply conduit and the fluid supply conduit passing therethrough into the chamber.

5. A suction device of claim 1, further comprising at least one spring-biased valve mechanism configured to normally close the vacuum supply conduit.

6. A suction device of claim 5, wherein the chamber is further configured to pass a fluid supply conduit.

7. A suction device of claim 6, further comprising a second spring-biased valve mechanism configured to normally close the fluid supply conduit.

8. A suction device of claim 1, wherein a proximal end of the body is configured to form an airtight seal around the vacuum supply conduit passing therethrough into the chamber.

9. A suction device of claim 1, wherein a proximal end of the hand grippable body is configured to form an airtight seal around the vacuum supply conduit and fluid supply conduit passing therethrough into the chamber.

10. A suction device of claim 1, wherein the chamber has a proximal half that is volumetrically larger than a distal half of the chamber.

11. A suction device of claim 1, wherein the vacuum supply conduit, when coupled to the vacuum supply, forms the suction pressure within a proximal half of the chamber located proximal to the location.

12. A suction device of claim 1, wherein the vacuum supply conduit forms the suction pressure at the location when the distal end of the outer cannula is covered by the fluid.

13. The suction device of claim 1, further comprising a vacuum connector configured to releasably couple the vacuum supply conduit to the suction tip.

14. A suction device handle to use with a vacuum supply conduit to suction a fluid or tissue, the handle comprising:
    a hand-grippable body defining a chamber and comprising a distal end configured to support a suction tip;
    the suction tip including a distal end of the vacuum supply conduit extending within an outer cannula, the vacuum supply conduit being offset from a distal end of the outer cannula by a predetermined distance and configured to couple to a vacuum supply, wherein the vacuum supply conduit includes a merging of an irrigation supply conduit and the vacuum supply conduit; and
    a connecting portion configured to couple the vacuum supply conduit to the suction tip;
    wherein the distal end of the body is configured to couple to a proximal end of the outer cannula and the chamber is configured to couple in fluid communication with suction pressure generated at the distal end of the vacuum supply conduit by the vacuum supply;
    wherein the vacuum supply conduit, when coupled to the vacuum supply, forms the suction pressure (a) at a location including within an annular space directly between an outer wall surface of the vacuum supply conduit and an inner wall surface of the outer cannula, (b) within a portion of the chamber located proximal to the location, and (c) that sucks fluid away from the outer cannula and into the vacuum supply conduit, wherein the annular space forms a passageway from the chamber to the distal end of the outer cannula, and the outer wall surface of the vacuum supply conduit and the inner wall surface of the outer cannula are offset from each other due to the annular space;
    wherein the vacuum supply conduit is configured to pass through the chamber into the suction tip.

15. A suction device of claim 14, further comprising a tip connector configured to releasably couple the distal end of the body to the suction tip.

16. A suction device of claim 14, wherein the chamber is further configured to pass a fluid supply conduit.

17. A suction device of claim 14, further comprising at least one spring-biased valve mechanism configured to normally close the vacuum supply conduit.

18. A suction device of claim 17, wherein the chamber is further configured to pass a fluid supply conduit.

19. A suction device of claim 18, wherein the suction device further comprises a second spring-biased valve mechanism configured to normally close the fluid supply conduit.

20. A suction device of claim 14, wherein a proximal end of the body is configured to form an airtight seal around the vacuum supply conduit passing therethrough into the chamber.

* * * * *